United States Patent [19]

Witzig

[11] 4,433,956

[45] Feb. 28, 1984

[54] ORTHOPEDIC CORRECTOR AND METHOD OF CORRECTION OF CLASS II MALOCCLUSION

[76] Inventor: John W. Witzig, 2040 N. Douglas Dr., Golden Valley, Minn. 55422

[21] Appl. No.: 374,440

[22] Filed: May 3, 1982

Related U.S. Application Data

[63] Continuation-in-part of Ser. No. 287,281, Jul. 27, 1981, abandoned.

[51] Int. Cl.³ ............................................. A61C 7/00
[52] U.S. Cl. ...................................................... 433/7
[58] Field of Search ............................................ 433/7

[56] References Cited

U.S. PATENT DOCUMENTS 4,239,487 12/1980 Murdock ................................. 433/7

FOREIGN PATENT DOCUMENTS 128350 7/1901 Fed. Rep. of Germany .......... 433/7

Primary Examiner—Robert Peshock
Attorney, Agent, or Firm—Malcolm Reid

[57] ABSTRACT

An improved orthopedic appliance for correcting a Class II malocclusion comprising an acrylic anterior segment molded to fit the lower mouth and dentition and two acrylic posterior segments molded to fit the upper mouth and dentition of a patient and an expansion screw connecting each posterior segment to the anterior segment for expandible movement between the anterior segment and the posterior segments. A method of correcting a Class II Division 1 malocclusion using an expandable but otherwise conventional orthopedic appliance. The appliance is expanded in stages to maximize the utilization of corrective lower jaw movements which result from the anchoring of the orthopedic appliance in the patient's upper mouth.

8 Claims, 3 Drawing Figures

ORTHOPEDIC CORRECTOR AND METHOD OF CORRECTION OF CLASS II MALOCCLUSION

CROSS REFERENCES TO CO-PENDING APPLICATIONS

Continuation in part of patent application entitled "Orthopedic Correction and Method of Correction of Class II Malocclusion," Ser. No. 287,281, filed July 27, 1981 and now abandoned.

BACKGROUND OF THE INVENTION AND SUMMARY

The present invention relates to an adjustable, functional and removable orthopedic corrector and, more particularly, to an improvement to conventional orthopedic correctors employed by orthodontists to correct what is referred to in the field of orthodontics as a Class II, Division 1, malocclusion. A Class II malocclusion is defined as a malposition of the maxillary and mandibular teeth so that the lower dental arch is posterior to the upper dental arch, resulting in loss of efficiency during the movements of the jaw that are essential for mastication. In a Class II, Division 1, malocclusion, the upper incisors are protruding.

Orthodontics is a specialty of dentistry dealing with the correction of positional irregularities of the teeth. These irregularities are often associated with a malpositioned lower jaw in relation to the maxillary dental arch. The lower jaw or mandible and concomitantly the mandibular dental arch, depending upon the class of malocclusion, is anterior or posterior to the maxillar arch.

The practice of orthodontics involves the procedures requiring, on the average, 24 to 30 months to complete, using fixed appliances commonly known as braces and somewhat less time using a conventional functional removable orthopedic appliance. In the case of the Class II, Division 1, malocclusion, most orthodontists that employ fixed appliances must resort to either extra oral force, intermaxillar elastics, or a combination of both, to effect a basal maxillo-mandibular change and thus eliminate the excessive overbite, overjet or apical base discrepancy. The orthodontist who uses the conventional removable functional appliances can eliminate the extra oral force or intermaxillary elastics by substituting neuromuscular activity. With a removable and functional orthopedic appliance, the entire mandible is moved forward, freeing the condyle in the temporal mandibular joint from any possible growth restrictions due to dominate retrusive muscular activity associated with the Class II, Division 1, malocclusion. This forward movement of the mandible is caused by a stretch reflex initiated by the introduction of the orthopedic appliance into a patient's mouth, which causes the muscles to pull the mandible in an anterior direction. The removable functional appliance is fitted to a patient's posterior maxillary teeth so that it is anchored in both a longitudinal and lateral direction by those teeth. The anterior portion of the appliance extends in an angular direction from the posterior portion of the appliance towards the back of the lower front teeth so that when the lower jaw is closed it is forced, due to the interdiction of the anterior portion of the appliance, to move to a position forward of the anterior portion of the appliance. The anterior portion of the appliance is designed so that it is forward of the posterior portion of the appliance to such a degree that the lower jaw must move forward of its pre-treatment position relative to the upper jaw. The appliance is held against the roof of the mouth by action of the tongue.

The present practice uses a series of two or more removable functional orthopedic appliances to correct a Class II, Division 1, malocclusion. As the treatment progresses and the mandible comes in closer alignment with the maxilla, the second or third of the series of functional removable appliances is used by the patient. Each successive appliance is elongated along an anterior-posterior medial line relative to the previously used appliance. With each successive appliance the mandible is repositioned more closely to a correctly aligned state relative to the maxilla. It would be desirable to be able to use a single appliance for the sake of economy. However, a single appliance would necessitate a design which would cause the mandible to be positioned at or near what is termed the construction bite at the onset of treatment. The construction bite is defined as the maximum forward movement of the mandible which the patient can self induce prior to treatment. Such abrupt and continuous forward movement of the mandible by the orthopedic appliance would result in discomfort to the patient and possible periodontal neucrosis and root resorption.

The present invention improves the conventional orthopedic appliance by removing the necessity of using two or more separate orthopedic appliances to treat a given patient. The present invention solves this problem by dividing the appliance into an anterior segment and posterior segment. The two segments are connected by two expansion screw assemblies.

The orthopedic appliance of the present invention is designed so that even when the posterior and anterior segments of the appliance are minimally expanded, the mandibular-maxilla position is changed from that which exists prior to treatment. As time progresses, the expansion screw assemblies are turned, separating the anterior and posterior segments of the appliance with resultant movement of the mandible more forward.

The orthopedic corrector of the present invention may also be outfitted with various orthodontic attachments such as a labial archwire. With the addition of various orthodontic attachments, the orthodontist can correct the Class II, Division 1, malocclusion and, in addition, induce the movement of individual teeth.

IN THE DRAWINGS

DESCRIPTION OF A PREFERRED EMBODIMENT

Figure 1:
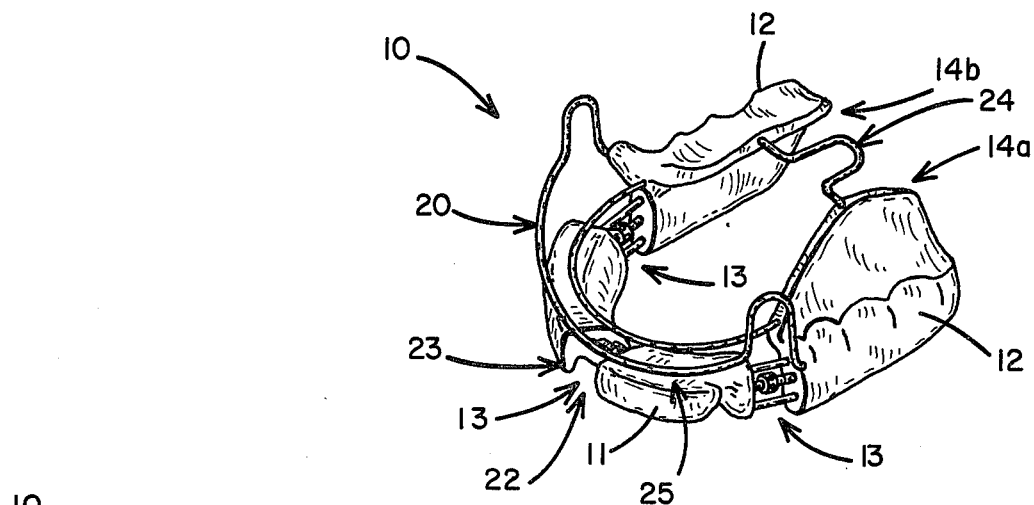
FIG. 1 is a diagrammatic perspective view of an orthopedic appliance of the present invention looking from the upper anterior portion of the orthopedic appliance.
Figure 3:
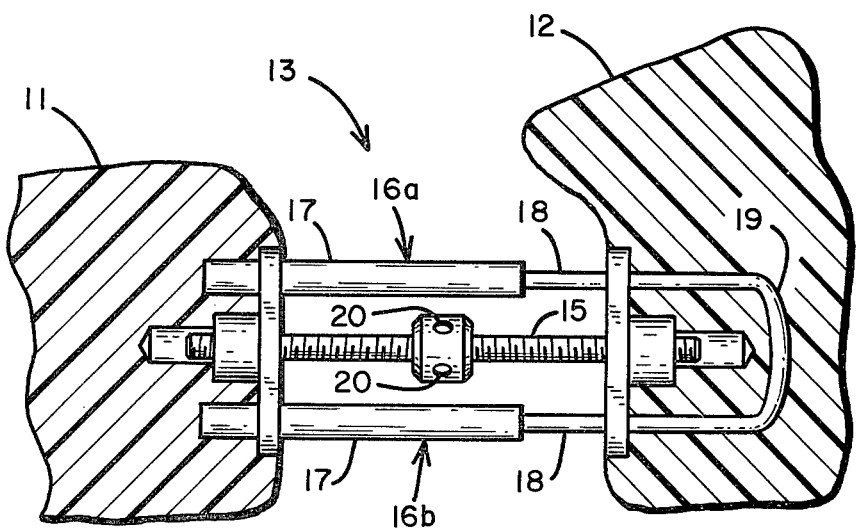
FIG. 3 is a planar view of an expansion screw assembly.

Referring to the drawings, there is shown in FIG. 1 an orthodontic appliance indicated generally at 10 according to the present invention. Both the anterior segment 11 and the posterior segment 12 are made of acrylic. Each segment 11 and 12 is molded to conform to a patient's mouth, using established techniques of the dental laboratory. With one such technique a plaster cast is made of a patient's mouth and dentition in the construction bite position. The orthopedic appliance 10 is molded, using the shape taken from the plaster cast. The mold used to make the acrylic orthopedic appliance 10 is designed so that the anterior segment 11 of the appliance 10 will be separated from the posterior segment 12. Expansion screw assemblies indicated generally at 13 in FIG. 3 are placed in the mold at the desired location and during the molding process are embedded into place in the acrylic. The expansion screw assemblies 13a and 13b are located on the sides 14a and 14b of the orthopedic appliance 10 as shown in FIG. 1. Both sides 14a and 14b of the posterior segment 12 are connected by reinforcement wire 24. Reinforcement wire 24 maintains the desired lateral separation between sides 14a and 14b of posterior segment 12. In addition to the expansion screw assemblies 13a and 13b, the orthopedic appliance 10 may include conventional elements such as a labial archwire 20, a lingual archwire 21, or an arch expansion screw 13c. Such conventional elements or combinations of them can be used to cause buccal, labial, rotational and lingual movement of individual teeth while the dominant effect of the orthopedic appliance 10 is at work; that is, influencing the mandible to move from a Class II malocclusion to a Class I Occlusion. Reinforcement wire 24, labial archwire 20 and lingual archwire 21 are each constructed of stainless steel chromiumnickel alloys and nonferrous metals.

Figure 2:
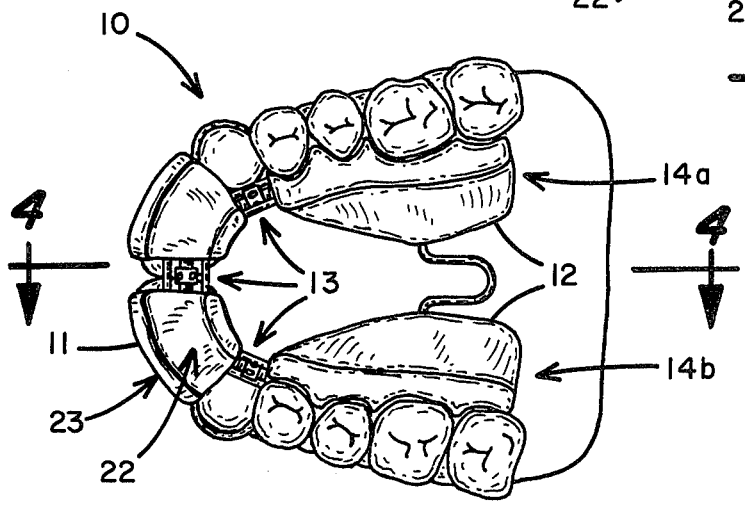
FIG. 2 is a diagrammatic perspective view of an orthopedic appliance of the present invention seated in the upper mouth of a patient.

FIG. 2 shows the placement of the orthopedic appliance 10 in the maxilla.

FIG. 3 shows the double guided expansion screw asssembly 13, which consists of an expansion screw 15 which is essentially a turnbuckle, and two guide post cylinders 16a and 16b. The expansion screw assembly 13 is a conventional and commercially available product. Double guided expansion screw assemblies 13 of the type used in the preferred embodiment are manufactured by Bernhard Forster GmbH of Germany and other companies. The Bernhard Forster screw carries the registered trademark "Forestadent". Expansion screw asssemblies 13 of this variety are made of stainless steel chromium-nickel alloys and nonferrous metals, thereby providing resistance against oral acidity. The guide post cylinders 16a and 16b provide resistance against forces tending to move the connected segments out of alignment with one another. The guide post cylinders 16a and 16b consist of a cylinder 17 and a concentrically movable piston 18. The guide post cylinders 16a and 16b are held together for alignment purposes by alignment wire 19. These commercially available expansion screw assemblies 13 are marked with an arrow indicating opening directions.

Figure 4:
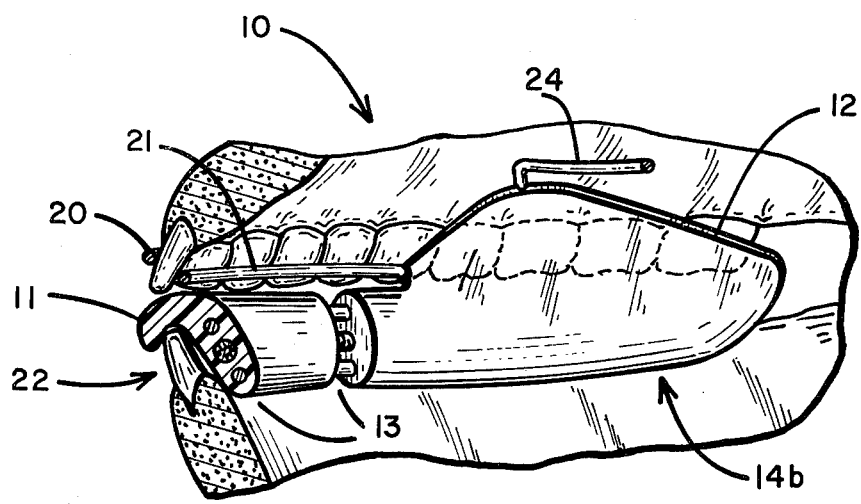
FIG. 4 is a cut-away view along line AA as shown in FIG. 3 of an orthopedic appliance of the present invention shown seated in the upper and lower mouth of a patient.

FIG. 4 is a cutaway view along line AA as shown in FIG. 3 of the orthopedic appliance of the present invention shown seated in the upper and lower mouth of a patient. The posterior end 12 is molded so that the lower portion of the sides 14a and 14b are molded to fit the inner contours of the patient's upper teeth. Only the rearward teeth are engaged by the mating contours of the lower portions of sides 14a and 14b. The mating engagement ceases at and does not include the canine teeth. The upper portion of sides 14a and 14b of the posterior segment 12 are molded to fit the roof of the patient's upper mouth. Anterior portion 11 is positioned in a downward angular relationship to posterior segment 12 so that the lower front teeth contact the back side of lip 23 when the mouth is in a closed position. Ramp 22 angles upwardly from the lower mouth towards the upper mouth with its apex joining the back wall of lip 23. The top of anterior segment 11 or the ridge 25 is molded so that the premaxillary teeth engage it when the mouth is closed.

DESCRIPTION OF OPERATION OF PREFERRED EMBODIMENT

The orthopedic appliance 10 is as its name implies—a device for orthopedic correction as opposed to orthodontic correction. The appliance can be outfitted with various conventional elements to accomplish orthodontic correction during the same period of time that orthopedic correction is taking place. Naturally, it is more economical to accomplish both corrections concurrently and preferable from the patient's point of view.

After the orthopedic appliance 10 has been molded to fit the individual patient's mouth by conventionally used techniques, the orthopedic appliance 10 is placed in the roof of the patient's mouth. It is held against the roof of the mouth by the patient's tongue. It must be emphasized that an orthopedic appliance 10 is a device which must be specially made to fit each individual's mouth. The patient wears the orthopedic appliance 10 with the posterior segment 12 expansion screw assemblies 13 fully closed for the first three months. Even with the posterior segment 12 fully closed, the orthopedic appliance of the present invention is molded so that when the mandible is in a closed position it will be forced slightly forward to its pre-treatment position relative to the maxillary arch. The posterior segment 12 is anchored in a predetermined position in the maxillary arch when the orthopedic appliance 10 is placed in the patient's mouth due to the mating engagement of the lower portions of the sides 14a and 14b of the posterior segment 12 with the inside contours of the upper molars of the patient. The anterior segment 11 is molded and connected to the posterior segment 12 by expansion screw assemblies 13 so that the back side of lip 23 is in mating engagement with the front side of the front teeth of the mandible when the lower jaw is closed. The lower front teeth are positioned at the apex of ramp 22 when the lower jaw is closed because ramp 22 causes the teeth to slide forward and upward along angular ramp 22 until they reach the apex of ramp 22. The back side of lip 23 maintains the front teeth of the lower jaw in a vertical position due to the vertically molded back side of lip 23. Labial archwire 20 and lingual archwire 21 tend to further anchor posterior segment 23 to the maxillary arch. The preferred embodiment uses these archwires but their inclusion is not necessary to accomplish the effective anchoring of the posterior segment 12 to the maxilla. Alternately, only the labial archwire 20 can be used to help arrest any backward movement of the posterior segment 23 of the orthopedic appliance 10. The more compelling reason for including the optional archwires 20 and 21 is to accomplish the orthodontic retrusion of protruding premaxillary teeth during the predominate effort of orthopedic correction of a retracted mandible. Labial archwire 20 is adjusted during the treatment process to gradually retrude the protruded premaxillary teeth as is conventionally done while lingual archwire 21 maintains the overall curvature of the premaxilla arch.

Expansion screw assembly 12 in the anterior segment 11 is a further optional element. The orthopedic appliance 10 of the present invention need not employ this expansion screw assembly 13, but may have an anterior segment 11 which is comprised of a single solid piece of acrylic material. Expansion screw assembly 12 in the anterior segment 11 may be used by the orthodontists to expand the maxilla arch laterally and is illustrated merely to point out the adaptability of the present invention to use with other elements to accomplish various treatment objectives simultaneously.

After the passage of the three month period, the patient is instructed to remove the orthopedic appliance 10 and, using a small tool supplied to the patient (the tool is simply a small straight thin rod supplied by the manufacturer of the expansion screw assembly 13), to turn each expansion screw assembly 13 on sides 14a and 14b of posterior segment 12 360° (four 90° turns), which results in approximately one millimeter of expansion. The guide post cylinders 16a and 16b serve an additional function of allowing the expansion screw 15 to be turned a maximum of 90°. The tool used to turn these expansion screws 15 hits the guide post cylinders 16a and 16b after a 90° turn and stops further movement. Any further turning of the expansion screw 15 must be accomplished by reinserting the tool into the other expansion screw tool insert guideway which is located on the expansion screw 15. Each successive week for a total of five weeks, the patient turns the expansion screw 15 approximately one millimeter per week, resulting in an aggregate of approximately five millimeters of expansion between the anterior segment 11 and the posterior segment 12 at full expansion. Five millimeters is the maximum expansion of the expansion screw assembly 13. When full expansion is reached, the lower jaw or mandible has, through a series of successively more forward positions relative to the maxilla, been forced to a position beyond the construction bite. The orthopedic appliance 10 must usually be worn by the patient for approximately twelve months to achieve the result of a Class I occlusion. During this period, the upper teeth are moving posteriorly relative to the mandible and the mandible is moving forward.

Although to achieve complete and stable conversion from a Class II malocclusion to a Class I occlusion it generally takes twelve months, studies conducted by researchers at the Center for Human Growth and Development, University of Michigan, Ann Arbor, Mich., using primate subjects, indicate that after insertion of an orthopedic appliance, corrective jaw movement begins almost immediately. During the first few days, no distinct change in muscle function occurs. However, after a subject learns to adapt to an orthopedic appliance an alteration in the pattern of the muscle formation and function gradually appears. The most dramatic change is observed in the superior head of the lateral pterygoid muscle. After two to four weeks an increase in the muscle changes occurs. This increase in muscular activity peaks at four to eight weeks after orthopedic appliance insertion. Gradually thereafter the pattern of muscle activity returns to the pretreatment level.

It was also found that the rate of growth within the mandibular condyle varies according to the time interval after orthopedic appliance insertion. The increased growth rate occurs during the first three months, with a peak occurring in the second month. After the initial three month period, when the rate of skeletal growth decreases, it appears to the researchers that structural balance is restored.

The present invention is designed to take advantage of these muscular and structural growth rates. During the initial three month period after insertion of the present invention, there is rapid change in both the mandibular condyle and muscle function. Due to the position of the anterior segment 11 of the orthopedic appliance 10 beyond the previously established position of the mandible, the skeletal and muscular growth changes result in permanent movement anteriorly of the mandible relative to the maxilla. This anterior movement of the mandible even occurs with the expansion screw assemblies 13 in sides 14a and 14b of posterior segment 12 closed. After the initial three month period, the growth rate decreases markedly and if a new appliance were not inserted which was designed to move the mandible beyond its new stabilized position, any further correction of the mandibular position would cease. The orthopedic appliance 10 of the present invention is designed to allow further modification of the jaw position in a series of steps by making one millimeter sagital expansions of the orthopedic appliance 10 every seven days, commencing with the end of the initial three months after insertion of the orthopedic appliance 10. The gradual expansions avoid patient discomfort and possible periodontal necrosis and root resorption which might result from an immediate expansion to the maximum extent allowed by the expansion screw assemblies 13 in sides 14a and 14b of posterior segment 12.

After the treatment period is completed and the orthopedic appliance 10 is no longer used by the patient, the mandible generally moves posteriorly about one millimeter which generally results in full correction of the mandibular-maxilla relationship.

The patient is instructed to wear the orthopedic appliance 10 at all times during the treatment period, except when eating, engaging in active sports and brushing the patient's teeth. The orthopedic appliance 10 is designed so that each time the patient moves his jaws, swallows or talks, he activates the orthopedic appliance 10 which exerts gentle pressure on the teeth and dental arches. The orthopedic appliance 10 is designed to fit loosely in the mouth and be capable of easy and frequent removal and replacement in the mouth by the patient, much like a dental plate. The looseness helps to encourage the patient to close his jaws together in the new relationship.

With the use of the orthopedic appliance 10 it is generally not necessary to use retention means after treatment is completed.

Lip 23 retards outward turning of the upper portions of the mandibular front teeeth during the treatment process. Due to the force which is exerted on the lower jaw by the anterior segment 11 during the successive extensions of the anterior segment 11 relative to the posterior segment 12 during the treatment period, the upper portions of the mandibular front teeth often rotate outwardly relative to their lower portions. The vertical back surface of lip 23 prevents this outward rotation. Lip 23 is another optional feature which can be added to the present invention as the treating orthodontist dictates. It is not necessary to the accomplishment of the dominate objective of the present invention which is the orthopedic correction of the mandible relative to the maxilla. Using the method of treatment of the current invention, the lip is cut off the orthopedic appliance 10 near the end of the treatment process, thereby allowing the maxilla and mandible to close completely in its final post treatment relationship. Previous to the removal of lip 23, the biting surfaces of the premaxillary teeth came to rest on the shelf 25.

The embodiments of the invention in which an exclusive property or privilege is claimed are defined as follows:

1. An orthopedic appliance for correcting a Class II, Division I, malocclusion comprising:
   a. a posterior segment having contoured sides for mating and longitudinally fixed engagement with the interior sides of a person's upper molars;
   b. an anterior segment having a contoured leading edge for mating engagement with the inside of the frontal arch of the person's mandible, the leading edge being a ramp which extends angularly outward in a direction from the bottom of the mandible to the top of the mandibular frontal arch, and
   c. an expansion screw assembly connecting the posterior and anterior segment for longitudinally expandible movement between the anterior segment and the posterior segment.

2. The orthopedic appliance of claim 1 wherein the leading edge of anterior segment has a lip which extends over and in front of the biting surface of the teeth of a person's mandibular frontal arch.

3. The orthopedic appliance of claim 1 wherein the posterior segment is comprised of two segments held in a laterally spaced relationship by a reinforcement wire laterally connected between the two posterior segments.

4. The orthopedic appliance of claim 1 wherein the anterior and posterior segments are fabricated from acrylic.

5. The orthopedic appliance of claim 1 wherein the expansion screw assembly includes an expansion screw and two guide post cylinders mounted above and below the expansion screw for maintaining alignment along an anterior-posterior line.

6. The orthopedic appliance of claim 1 wherein the expansion screw assembly is fabricated of stainless steel chromium-nickel alloys and nonferrous metals.

7. A method of influencing the mandible of a human patient to move from a Class II, Division I, malocclusion to a Class I occlusion which comprises:
   forming an orthopedic appliance molded to fit the mouth and dentition of the patient to be treated while the patient's lower jaw is held in a construction bite position, said orthopedic appliance comprising an anterior segment and a posterior segment, the posterior segment being expandably connected along a longitudinal line to the anterior segment by an expansion screw assembly, the posterior segment having contoured sides for mating and longitudinally fixed engagement with the interior sides of the patient's upper molars, and the anterior segment having a contoured leading edge for mating engagement with the inside of the frontal arch of the patient's mandible, the leading edge being a ramp which extends angularly outward in a direction from the bottom of the mandible to the top of the mandibular frontal arch;
   inserting the orthopedic appliance in the patient's mouth in the minimally expanded position for a period of three months;
   removing the appliance and expanding it by use of the expansion screw assemblies approximately one millimeter and reinserting it in the patient's mouth for one week and therafter repeating this process each successive week for a total of five weeks; and
   after expanding the appliance each successive week for a total of five weeks, wearing the appliance in the patient's mouth for approximately 12 months until the result of a Class I occlusion is achieved.

8. The orthopedic appliance of claim 1, also comprising lingual and labial archwires attached to each side of the posterior segment for additional anchoring of the posterior segment to the maxilla.

* * * * *